United States Patent

Coutel et al.

Patent Number: 5,417,985
Date of Patent: May 23, 1995

[54] SOLID AND POROUS SINGLE DOSAGE FORM COMPRISING PARTICLES IN THE FORM OF BEADS AND ITS PREPARATION

[75] Inventors: Anne Coutel, Antony; Guy Lebreton, Gif sur Yvette; Michel Veillard, Sceaux, all of France

[73] Assignee: Farmalyoc, France

[21] Appl. No.: 57,407

[22] Filed: May 6, 1993

Related U.S. Application Data

[63] Continuation of Ser. No. 642,946, Jan. 18, 1991, abandoned, and a continuation-in-part of Ser. No. 835,012, Feb. 12, 1992, Pat. No. 5,384,124, each is a continuation of Ser. No. 382,286, Jul. 20, 1989, abandoned.

[30] Foreign Application Priority Data

Jan. 19, 1990 [FR] France .................. 90 00624

[51] Int. Cl.$^6$ ............................................. A61K 9/14
[52] U.S. Cl. ............................ 424/489; 424/458
[58] Field of Search ............. 424/489, 490, 497, 430, 424/436, 422, 441, 458, 465, 464; 264/5, 13, 14, 6

[56] References Cited

U.S. PATENT DOCUMENTS

| | | | |
|---|---|---|---|
| 3,328,256 | 6/1967 | Gaunt | 264/5 |
| 3,341,415 | 9/1967 | Scott | 264/6 |
| 3,433,872 | 3/1969 | De Ritter et al. | 514/263 |
| 3,445,563 | 5/1969 | Clegg et al. | 264/5 |
| 3,951,821 | 4/1976 | Davidson | 424/465 |
| 4,086,346 | 4/1978 | Böcker et al. | 264/5 |
| 4,151,274 | 4/1979 | Schlueter et al. | 264/5 |
| 4,231,227 | 11/1980 | Stewart et al. | 264/14 |
| 4,238,429 | 12/1980 | Sasaki et al. | 425/6 |
| 4,389,356 | 6/1983 | Higgins | 264/13 |
| 4,414,016 | 11/1983 | Orlander et al. | 264/5 |
| 4,684,534 | 8/1987 | Valentine | 424/441 |
| 4,748,024 | 5/1988 | Leonard | 424/489 |
| 4,790,991 | 12/1988 | Shaw et al. | 424/441 |
| 4,793,783 | 12/1988 | Huey et al. | 425/10 |
| 4,818,279 | 4/1989 | Chaleat et al. | 425/6 |
| 4,892,734 | 1/1990 | Leonard | 424/422 |
| 4,915,949 | 4/1990 | Wong et al. | 424/458 |
| 4,935,173 | 6/1990 | Huey et al. | 264/14 |
| 5,051,261 | 9/1991 | McGinity et al. | 424/464 |
| 5,093,128 | 3/1992 | Deaguesku et al. | 424/489 |

FOREIGN PATENT DOCUMENTS 352190  1/1990  European Pat. Off. .
2613223  7/1988  France .

Primary Examiner—Thurman K. Page
Assistant Examiner—Wm. Benston
Attorney, Agent, or Firm—Morgan & Finnegan

[57] ABSTRACT

This invention relates to new solid and porous single dosage form comprising beads and its preparation.

This new solid single dosage form applies to the administration of therapeutically active substances, nutrition agents, diagnostic agents or cosmetic agents.

18 Claims, 1 Drawing Sheet

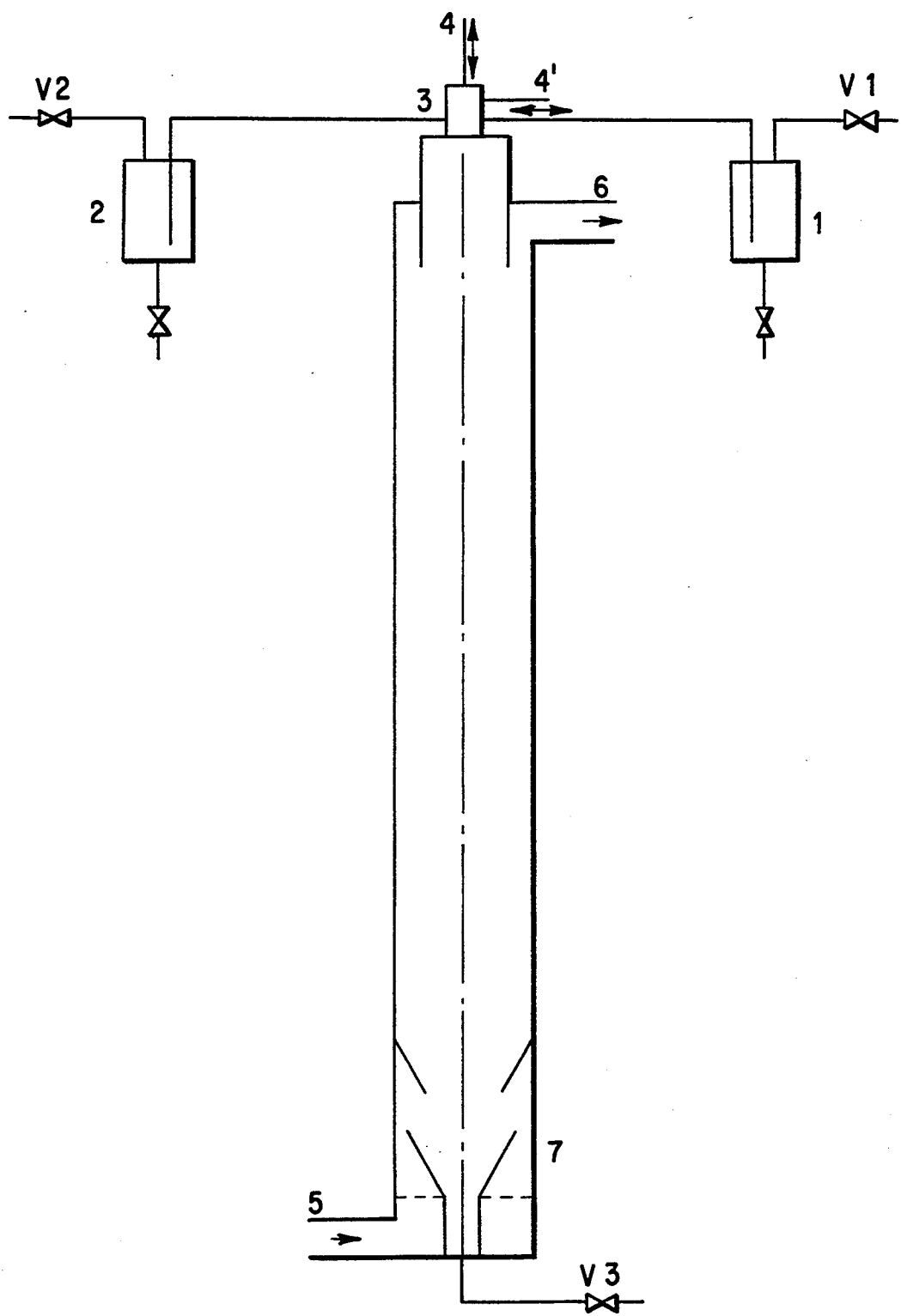

SOLID AND POROUS SINGLE DOSAGE FORM COMPRISING PARTICLES IN THE FORM OF BEADS AND ITS PREPARATION

This is a continuation of application Ser. No. 07/642,946, filed on Jan. 18, 1991, now abandoned, which is a continuation of application Ser. No. 07/382,286, filed Jul. 20, 1989, now abandoned.

This is also a continuation-in-part of application Ser. No. 07/835,012, filed on Feb. 12, 1992, now U.S. Pat. No. 5,384,124, which is a continuation of application Ser. No. 07/382,286, filed Jul. 20, 1989, now abandoned, all hereby incorporated by reference.

FIELD OF THE INVENTION

The present invention relates to a new solid and porous single dosage form comprising particles in the form of beads and the process for its preparation.

BACKGROUND OF THE INVENTION

The preparation of microparticles is mainly used so as to delay the dissolution of active principles and, because of this, finds numerous applications in the field of controlled-release medicaments and in the field of masking the taste of medicaments intended for oral administration. However, it has always been difficult to develop a formulation containing microparticles in the form of unit doses and in particular a formulation suitable for oral administration.

In fact, the industrial preparation of tablets and capsules requires free-flowing and/or cohesion properties of the granule to be subdivided, which the microparticles do not necessarily possess.

The tablet presents problems of the integrity of the microparticles under the effect of the compression; its slow rate of disintegration does not always allow it to be administered after disintegration and suspending in a glass of water.

The capsule does not always allow the dispersion of the particles in the gastrointestinal tract.

Moreover, both the capsule and the tablet present problems in swallowing, which are particularly pronounced in children and old people.

Finally, the sachet is an expensive pharmaceutical form, for non-ambulant use and the dry syrup form can frequently not be produced for reasons of early liberation of the active principle out of the microparticles or physical and/or chemical stability of the preparation.

The production of beads, better known in the prior art under the term prills, is described in the patents European Patent No. 277,508, U.S. Pat. Nos. 4,525,198 and 4,389,356. Unfortunately, the processes for the preparation of these beads are not applicable to all products.

These processes are used for products which can be subjected to sudden heating intended to render them molten and to rapid cooling to ensure their solidification. On the other hand, they are of poor suitability for the pharmaceutical industry which uses regular bead sizes of the order of a few tens to a few hundred microns are desired.

French Patents 2 036 890 and 2 366 835 describe pharmaceutical forms having the characteristic of rapidly dissolving or disintegrating in an aqueous medium or in the saliva.

It has now been found that techniques having totally opposed aims, such as delaying the dissolution of an active principle on the one hand and the fact that the pharmaceutical form rapidly disintegrates or dissolves on the other hand, can be combined in such a way as to obtain a lyophilized single dosage form, which is able to disintegrate easily and rapidly in water, which contains the active principle in the form of beads and in which settling and/or rising to the surface of the particles during lyophilization has been prevented.

BRIEF DESCRIPTION OF THE DRAWING

FIG. 1 is a schematic representation of equipment useful in the practice of the present invention.

DESCRIPTION OF THE INVENTION

According to the invention, the process for the preparation of the new solid single dosage form consists in 1) preparing a mixture of beads containing a predetermined amount of one or more active principles, 2) incorporating the mixture obtained into a paste intended to be lyophilized and containing
   a) at least one substance chosen from thickening and structuring substances serving as carrier and ballasts,
   b) one or more stabilizers preventing the settling and/or rising to the surface of the beads in the mixture,
   c) optionally, one or more other active principles or mixtures of beads containing an active principle, and
   d) a suitable amount of water in order to adjust the viscosity of the composition, and 3) lyophilizing the paste obtained.

The lyophilized product obtained can be subdivided mechanically into unit doses having a well-defined shape and volume, but it is preferable to portion out the paste into cells of predetermined shape and size before the lyophilization operation, the amount of the active principle or principles in the paste and the shape and the sizes of the cells being calculated so as to obtain a precisely defined amount of the active principle or principles in each unit dose.

In the above description, and in the text which follows, "active principle" is understood to mean any substance containing at least one therapeutically active product, a nutrition agent, a diagnostic agent or a cosmetic agent, which may be in combination with one or more other substances of the same type or in combination with other mixtures of beads themselves containing other substances mentioned above.

The mixture of beads containing a predetermined amount of active principle is prepared by an original method which avoids having recourse to very intensive cooling or to towers of too great a height.

In fact, some active principles exhibit so-called "supercooling" phenomena during their melting, which considerably delay their solidification even after cooling. It is now possible to carry out the shaping of regular spheres whatever the active principle, including in the case of active principles which have a non-defined crystallization point (or more commonly a supercooling phenomenon) and which therefore are not very favorable for the "prilling" technique since they have the tendency to remain in the oily or pasty form even after a return to a temperature below their melting point.

The method for the preparation of beads comprises mixing the active principle with one or more excipients in molten form, forcing the passage of the molten mass through a nozzle which is subject to vibration, allowing the beads formed to fall in a tower in counter-current with a gas and collecting the solid beads at the bottom of the tower.

A fluidized bed is optionally attached to this prilling tower, which fluidized bed enables the beads which are still not completely solidified to be kept in permanent fluidization.

The additives which enable the crystallization of the product to be induced are chosen from one or more products which are inert towards the said active principle, in particular:

fatty alcohols, such as:
  cetyl alcohol or
  stearyl alcohol,
fatty acids, such as:
  stearic acid or
  palmitic acid,
glycerol esters, such as:
  glycerol palmitostearate,
  the glycerol stearate marketed under the name:

PRECIROL or
the glycerol behenate marketed under the name:

COMPRITOL hydrogenated oils, such as:
  the hydrogenated castor oil marketed under the name:

CUTINA HR the salts of fatty acids, such as:
  magnesium stearate or calcium stearate,
polyols, such as:
  mannitol,
  sorbitol or
  xylitol,
waxes, such as:
  white wax,
  Carnauba wax or
  paraffin,
polyoxyethylene glycols of high molecular weight, and
esterified polyoxyethylenes, such as:
  PEG-32 distearate or
  PEG-150 distearate.

It is sometimes desirable to add to these crystallization additives polymers which are soluble or dispersible in the molten mass and which will permit a controlled dissolution, which can be modulated, of the beads during their use, such as:

cellulose derivatives (hydroxypropylcellulose, hydroxypropylmethylcellulose, hydroxyethylcellulose, ethylcellulose or carboxymethylcellulose),
acrylic resins (marketed under the name EUDRAGIT),
polyvinyl acetates (marketed under the name RHODOPAS), and
polyalkylene (ethylene propylene), polylactic, maleic anhydride or silicone resins.

Some inorganic additives, with the crystallization additives, allow the solidification of the active principles to be accelerated, in particular when said active principles exhibit a supercooling phenomenon. The following may be mentioned by way of example:
  silicas,
  inorganic oxides, such as titanium oxide or iron oxide,
  phosphates,
  carbonates,
  clays, and
  talc.

In order to improve the dispersion of the active principle in the crystallization additive, it is sometimes useful to add a surfactant chosen, for example, from sorbitol esters, the polyoxyethylene polysorbates marketed under the name TWEEN, and glycols such as glycerol or propylene glycol.

The process for the preparation of beads consists in preparing a molten mass of the active principle or principles with one or more excipients. This mass can be prepared by separate melting of the various constituents followed by their mixture or by melting of the mixture of the constituents, any insoluble compounds being added at the end of melting so as to obtain a homogeneous mass.

The nature of the constituents of the molten mass is chosen by those skilled in the art of the technique under consideration, depending on the compatibility of the constituents, the viscosity of the mixture of constituents, the diameter of the nozzle, the hydrophilic character of the active principle, the surface tension of the active principle, the particle size of the insoluble additives, the throughput of the nozzle, the temperature of the tower and its height and especially the size of the desired beads, the amount of active principle to be incorporated therein and the desired liberation time of the active principle.

The "in vitro" liberation and the "in vivo" availability of the active principle from these beads is modified (prolonged, delayed or postponed) by virtue of the crystallization additive which, depending on its nature, permits a liberation of the active principle in times which are two to twenty times longer than that for the same active principle made up in the conventional manner, for example in the form of tablets with immediate liberation. Thus, these beads permit medicaments prepared therefrom to be taken once a day, instead of 2 to 3 times a day with the conventional medicament with immediate liberation.

Among the crystallization additives which allow a delayed effect, the following may be mentioned, without any limitation being implied: fatty acids, glycerol esters, hydrogenated oils, waxes and esterified polyoxyethylene glycols.

The equipment is described more completely with reference to the appended FIG. 1. The active principle is introduced into the vessel 1 and the excipient into the vessel 2, or the molten mixture of excipient plus active principle is introduced into each of the two vessels. These two vessels are kept under an inert gas atmosphere. By means of two tubes, the molten liquids are brought above a nozzle which is kept in a non-cooled atmosphere and which may even be heated (3). The nozzle has 1 to 24 perforations or more, preferably having a diameter of between 50 and 600 microns. The length of the perforation is preferably between 0.5 and 10 times the diameter of the latter.

This nozzle is subjected to a high frequency (500 to 10,000 hertz) electrical vibration system (4). Cold air, which allows the solidification of the active principle and of the excipient, is introduced at the bottom of the tower (5) and leaves below the nozzle (6) at a distance which is preferably about L/10 relative to the top of the tower, L being the height of the tower.

Each orifice of the nozzle preferably has the shape of an inverted cone, the point of the cone being directed towards the bottom of the tower, which enables a perfectly laminar flow of liquid to be obtained.

The height of the tower varies between 1 meter and 10 meters and the tower can comprise, in the lower quarter of its height, a perforated skirt in the form of a truncated cone which centers the beads in the fluidized bed.

Within the framework of the present invention, the fluidized bed (7) which may be attached to the bottom of the tower is preferably a fluidized bed in the form of a funnel fitted at its base with a distribution grating enabling the adherence to the walls to be minimized and the wall/beads shocks to be promoted with the aim of increasing the solidification rate. The attachment of this type of equipment allows a more intensive solidification of the mixture of constituents in the sphere, the outside already being solid at the inlet to the fluidized bed.

The spheres or beads obtained by this process have a regular shape and a diameter of between 0.1 mm and 1.5 mm. The amount of active principle introduced varies from 5 to 95% by weight and preferably from 40 to 60% by weight.

The thickening and structuring substance which serves as a carrier in the preparation of the new single dosage form may be chosen from any substance which is soluble or dispersible in water and enables the cohesion of the mass to be ensured and which, if necessary, is acceptable from the pharmaceutical standpoint and inert towards the active principle. These substances are chosen, in particular, from polypeptides, such as gelatin or partially hydrolysed gelatin, colloids, polysaccharides of high molecular weight, polymers of high molecular weight which can give colloidal solutions, for example naturally occurring gums (gum arabic, gum tragacanth . . . ), synthetic or semi-synthetic gums (glycosylglucans, xanthan gum . . . ), dextran, dextrin, alginates (sodium alginate), pectinates, cellulose derivatives (microcrystalline cellulose, carboxymethylcellulose . . . ), starch derivatives dispersible in water, colloidal silicas, bentonites or other carrier substances such as polyvinyl alcohol, polyvinylpyrrolidone, polyethylene glycols (PEG 20,000 and PEG 6,000 in particular), acrylic polymers or copolymers or mixtures of substances as mentioned above.

Preferably, a water-soluble substance is used.

"Ballasts" are understood to be substances which are preferably soluble and crystallizable and, if necessary, pharmaceutically acceptable and which improve the physical properties of the new single dosage form. These substances may in particular be chosen from lactose, glycocoll, sorbitol, mannitol, glucose or maltodextrins or, if appropriate, from oxides (magnesium oxide), carbonates (calcium carbonate), phosphates (tricalcium phosphate) or microcrystalline cellulose, or mixtures of these substances.

It is understood that the paste intended for lyophilization must necessarily contain at least one substance chosen from the abovementioned thickening substances and ballasts, but it is also advantageous to use one or more thickening substances and one or more ballasts at the same time.

The thickening and structuring substances and the ballasts are chosen so as to confer on the paste intended for lyophilization a rheological behavior and a viscosity which are suited for a good subdivision of the product and for keeping the various components in suspension (free-flowing, homogeneity, regularity of the subdivided volume, stability of the suspension during the subdivision). These substances are also chosen so as to ensure the texture of the final lyophilized product (for example sufficient hardness to permit extrusion through a blister).

The paste intended for lyophilization must also contain one or more suspending agents intended to prevent the sedimentation of the particles during the lyophilization. These stabilizers are particulate solid substances of micron size which are inert towards the mixture. They may be either insoluble or soluble and in excess relative to the dissolving power of the paste to be lyophilized. They are chosen such that their sedimentation rate is of the same order of magnitude as those of the beads. Because of this, the choice of stabilizer is modified depending on the density and the size of the beads and on the pH conditions of the solution into which it is introduced. Amongst the suitable stabilizers, the following may be mentioned: oxides (titanium oxide, magnesium oxide, iron oxides or silica, for example), salts, such as carbonates (calcium carbonate or magnesium carbonate, for example), silicates (kaolin, for example), phosphates (tricalcium phosphate, for example) and sugars (lactose, glucose, mannitol, levulose or maltodextrin, for example).

In the process according to the invention, it is understood that the sequence in which the various substances are introduced depends on these substances themselves, some of which may be mixed beforehand.

In general, the thickening and structuring substances make up from 0.01 to 99% by weight relative to the solids content of the lyophilized product. It is also possible to introduce only ballasts and not to use any thickening substance.

The ballasts are generally in excess relative to the dissolving power of the paste to be lyophilized. They make up 1 to 99% by weight relative to the total solids content of the lyophilized product. It is, however, possible to introduce only the thickening substance, without using ballast.

The stabilizer depends on the particles which make up the paste to be lyophilized and represents from 1 to 70% by weight relative to the solids content of the lyophilized product.

The amount of water introduced is determined such that the paste to be lyophilized has a suitable rheological behavior and viscosity. In fact, it is desirable to adjust the viscosity of the paste to be lyophilized such that said paste is sufficiently fluid to permit a regular subdivision and sufficiently viscous to prevent sedimentation of the particles.

The amount of water introduced into the make-up of the mixture will be able to represent 10 to 90% by weight relative to the moist mass to be lyophilized, depending on the nature of the substances chosen to make up the mixture.

Finally, the mixture of beads containing the active principle or principles is prepared in such a way that the polymer or the macromolecular substance introduced represents 0.1 to 80% by weight relative to the solids content of the lyophilized product.

In addition, the preparation intended to be lyophilized may optionally contain other additives, such as, for example, surfactants, or other substances which are compatible and, if necessary, pharmaceutically acceptable, such as colorants, sweeteners or substances which modify the taste, preservatives or any other substance compatible with the remainder of the mixture.

By way of example, the surfactants can be chosen from nonionic agents [polyoxyethylene polysorbates (Tween), sorbitan esters (Span), ethylene oxide/propylene oxide copolymers, ethers of polyoxyethylene glycols and fatty alcohol . . . ], anionic agents [sulphosuccinic acid esters: dialkyl sulphosuccinates, for example sodium dioctylsulphosuccinate] and cationic agents (quaternary ammonium salts).

The sweeteners or substances modifying the taste can be, in particular, sucrose, glucose, xylose, sorbitol, saccharin, saccharinates, cyclamates, aspartane, ammonium glycyrrhizinate or citric, ascorbic or tartaric acid, or any other substance which is customarily used for the modification of the taste in the foodstuffs or pharmaceutical industry and which is compatible with the products brought into contact.

All of these substances may be added arbitrarily at the start, during or at the end of making up the paste to be lyophilized.

It is understood that this new solid single dosage form can be applied to the administration of all types of substances (whether or not these are substances exhibiting supercooling problems) and more particularly to the pharmaceutical active principles which can be used orally and are intended either for human medicine or for veterinary medicine. It also applies to nutrition agents, diagnostic agents and cosmetic agents.

By way of example, amongst the pharmaceutically active substances which can be administered in this form the following may be mentioned: anti-infection agents (spiramycin, pristinamycins, tetracyclines, metronidazole, pefloxacin and derivatives of the family of quinolones, cefixim, josamycin . . . ), anti-inflammatory and anti-rheumatic agents (ketoprofen, 2-(4-isobutylphenyl)propionic acid . . . ), analgesics (aspirin, paracetamol, clometacin . . . ), tranquilizers (lorazepam, oxazepam, meprobamate, zopiclone and other derivatives of the family of cyclopyrrolones, . . . ), cardiovascular agents and cerebral vasodilators (digoxin, quinacainol, propranolol, oxprenolol, vincamine, nicergoline . . . ), cerebral protectors (gangliosides, for example), antispasmodic and antisecretory agents, antiasthmatic agents, therapeutic agents for diseases of the gastrointestinal tract, hepatic protectors, hormones, contraceptives, medicaments intended for the treatment of allergies, vaccines, vitamins or peptides, polypeptides or proteins.

Among the nutrition agents, those which may be mentioned in particular are amino acids, for example methionine, lysine, carnitine lysinate . . .

The new solid single dosage form also applies to in vitro diagnostic agents, for example acridine orange (phagocytosis labeller) or to in vivo diagnostic agents.

When the new solid single dosage form is applied to cosmetic agents, the active principle is in particular chosen from the substances which modify the breath,. such as, for example, menthol and peppermint or eucalyptus essence.

The amount of active principle introduced is variable depending on its nature but it is of course understood that this new solid form can allow unit doses having a high active principle content to be prepared, thus allowing the number of times it has to be taken to be reduced, taking account of the controlled liberation of the said active principle. In general, the amount of active principle can be up to 95% by weight relative to the solids content.

The new solid form according to the invention thus has the advantage of uniting a primary single dosage form which disintegrates instantly in an aqueous medium with a secondary form showing controlled dissolution and consisting of a particulate system.

The primary form enables easier use, in particular prevents the agglomeration of particles and above all has the advantage of containing a predetermined amount of active principle.

The secondary form controls the liberation of the active principle in contact with aqueous media. It applies very particularly to the substances which are unstable in solution. For example, when the active principle is intended for oral administration, the shape of the particles enables the availability of the active principle to be controlled; the substance is protected until it reaches the desired zone or until the desired time and the liberation of the active substance is then associated with factors such as the pH, the ionic force, the presence of an enzyme and the presence of an unspecific or specific bacterial flora. The choice of the size of particles enables the rate of liberation of the active principle to be predetermined; for example, the rate of liberation in the gastro-intestinal medium when the active principle is administered orally. This secondary form may, of course, contain several series of particles which are either mixed with one another and from which the active substances will be liberated simultaneously or successively or are contained one in the other and from which the active substances will be liberated successively. The secondary form also makes it possible to mask the taste of active substances, for example bitter products.

For this reason, when it is applied to pharmaceutical formulations, the new solid single dosage form according to the invention is very particularly indicated for oral administration, but it can also be used for rectal or vaginal administration.

Taking account of the advantages which it offers, the new solid single dosage form according to the invention is very particularly indicated for the oral pharmaceutical formulations intended for pediatrics or geriatrics, for formulations for buccal bioadhesion, for example breath freshening systems . . . , for colonic vectorisation formulations . . . or in veterinary medicine, in the case of foodstuff adjuvants or in the case of medical diagnostics.

EXAMPLES

The following examples, given without any limitation being implied, illustrate the present invention.

EXAMPLE 1

| *Single dosage form: | |
|---|---|
| Beads containing 50% of ketoprofen | 200.00 mg |
| Xanthan gum | 0.75 mg |
| Sodium dioctylsulphosuccinate | 0.35 mg |
| Dextran 70 | 30.00 mg |
| Mannitol | 518.90 mg |
| Solids content per single dose | 750.00 mg |

Composition of the beads: 50% Précirol ®+50% ketoprofen

*Method:

The ketoprofen beads are mixed dry with mannitol in a planetary mixer.

The xanthan gum is dispersed in purified water (450.00 mg per unit dose) and the dextran 70 and the sodium dioctylsulphosuccinate are then dissolved. The solution thus obtained is added to the dry mixture. The pasty mixture is malaxated to obtain a homogeneous paste.

The paste obtained is divided into 1.2 cm polyvinyl chloride cells in amounts of 1.2 g per unit dose so as to obtain 100 mg of ketoprofen per dose.

The preparation is then frozen at a temperature below −30° C. and then lyophilized to remove the water from the preparation.

The lyophilized products obtained are then packaged by heat sealing in an aluminum foil 20 μm thick.

The lyocs thus obtained disintegrate in water within about 1 minute.

Preparation of the ketoprofen beads:

Beads containing 50% of ketoprofen and 50% of Précirol ® are prepared.

Operating conditions:
Nozzle diameter: 0.3 mm
Frequency of the vibrations: 4090 Hz
Nozzle temperature: 95° C.
Average diameter of the beads: 600 μm The ketoprofen and the Précirol ® are melted in a stirred reactor and then transferred to one or both pots.

Cooling air is admitted at a flow rate of 1.5 to 1.8 m/s.

The fluidized bed is brought into service.

When the outlet temperature of the air is the normal operating temperature, the valve $V_1$ or $V_2$ admits nitrogen under the chosen pressure and the liquid is transferred to the nozzle.

The frequency is adjusted by means of a generator, observing the beads visually with a stroboscope (if necessary the cooling air is aspirated through a bed of solid carbon dioxide so that it has a temperature of 4° to 12° C. before entering the tower).

The beads are recovered from the bottom of the tower; they have a hardness sufficient to be shaped pharmaceutically.

EXAMPLE 2

The procedure is as described above in Example 1, but the following constituents are used as starting materials:

| | |
|---|---|
| Beads containing 50% of ketoprofen | 200.00 mg |
| Xanthan gum | 0.75 mg |
| Sodium dioctylsulphosuccinate | 0.35 mg |
| Dextran 70 | 30.00 mg |
| Lactose | 518.9 mg |
| Solids content per single dose | 750.00 mg |

The lyophilized products obtained disintegrate in water within about 1 minute.

The ketoprofen beads are prepared as described above in Example 1.

EXAMPLE 3

The procedure is carried out as described in Example 1, but using the following constituents as starting materials:

| | |
|---|---|
| Beads containing 50% of ketoprofen | 200.00 mg |
| Xanthan gum | 0.75 mg |
| Sodium dioctylsulphosuccinate | 0.35 mg |
| Dextran 70 | 50.00 mg |
| Peppermint flavor | 3.50 mg |
| Sodium saccharinate | 2.00 mg |
| Mannitol | 493.40 mg |
| Solids content per single dose | 750.00 mg |

The peppermint flavor and the sodium saccharinate impart an agreeable taste to the preparation, which can easily be administered without prior disintegration in a glass of water.

The ketoprofen beads are prepared as described above in Example 1.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A solid and porous single dosage composition able to disintegrate easily in water and suitable for taste masking and controlled release obtained by
   1) preparation of a mixture of structurally homogenous beads containing a predetermined amount from the group consisting of at least one therapeutically nutrient, diagnostic, and cosmetic as an active principle calculated so as to obtain a defined amount of the active principle or principles in each single dose, wherein the active principle is selected from the group consisting of compounds having a non-defined crystallization point and wherein the amount of active principle is present in an amount of up to by weight relative to the solid content,
   2) incorporation of the prepared mixture into a paste intended to be lyophilized, said paste comprising
      a) at least one substance selected from the group consisting of
         thickening and structuring substances serving as a carrier and
         ballast selected from the group consisting of lactose, glycocolls, sorbitols, mannitols, glucose, maltodextrins, oxides, carbonates, phosphates, microcrystalline cellulose, and mixtures thereof,
      b) at least one stabilizer selected from the group consisting of oxides, salts such as carbonates, silicates, phosphates, and sugars, which reduces the tendency of the beads from settling and/or rising to the surface in the paste,
      c) optionally, at least one other active principle or mixture of particles comprising an active principle, and
      d) a suitable amount of water in order to adjust the viscosity of the composition, and
   3) lyophilization of the paste obtained.

2. The composition of claim 1, wherein the paste is portioned out into cells of predetermined shape and size prior to lyophilization calculated so as to obtain a defined amount of the active principle or principles in each single dose.

3. The composition of claim 1, wherein the lyophilized product is divided into single dosages of predetermined shape and size calculated so as to obtain a defined amount of the active principle or principles in each single dose.

4. The composition of claim 1, further containing a surfactant selected from nonionic, anionic and cationic agents and mixtures thereof.

5. The composition of claim 1, further containing substances modifying the taste selected from sweeteners and flavorings.

6. The composition of claim 1, containing a first portion which disintegrates rapidly in an aqueous medium to release one or more active principles and a second portion which delays release of one or more active principles over predetermined periods of time.

7. The composition of claim 1, wherein a thickening and structuring substance is soluble or dispersible in water and promotes the cohesion of the beads of active principle.

8. The composition of claim 1, wherein a thickening and structuring substance promotes the formation of a colloid or colloidal solution containing the beads of active principle.

9. The composition of claim 1, wherein a thickening and structuring substance is selected from the group consisting of polypeptides, polysaccharides, gums, starch derivatives dispersible in water, colloidal silicas.

10. The composition of claim 1, wherein a thickening and structuring substance is selected from the group consisting a pharmaceutically acceptable polymers of high molecular weight.

11. The composition of claim 1, wherein the ballast is water soluble and crystallizable.

12. The solid and porous single dosage form composition according to claim 1, comprising an oral administrable composition.

13. The solid and porous single dosage form composition according to claim 1, comprising a rectally or vaginally administrable composition.

14. The solid and porous single dosage form composition according to claim 1, wherein the active principle is therapeutic.

15. The solid and porous single dosage composition according to claim 1, which is administrable to animals.

16. A process for the preparation of a solid and porous single dosage form composition, able to disintegrate easily in water and suitable for taste masking and controlled release which comprises
1) preparing a mixture of structurally homogenous beads containing a predetermined amount from the group consisting of at least one therpeutically active product, nutrient, diagnostic, and cosmetic as an active principle calculated so as to obtain a defined amount of the active principle or principles in each single dose, wherein the active principle is selected from the group consisting of compounds having a non-defined crystallization point and wherein the amount of active principle is present in an amount of up to 95% by weight relative to the solid content,
2) incorporating the mixture obtained in a paste intended to be lyophilized, said paste comprising
   a) at least one substance selected from the group consisting of
      thickening and structuring substances serving as a carrier and
      ballasts selected from the group consisting of lactose, glycocolls, sorbitols, mannitols, glucose, maltodextrins, oxides, carbonates, phosphates, microcrystalline cellulose, and mixtures thereof,
   b) at least one stabilizer selected from the group consisting of oxides, salts such as carbonates, silicates, phosphates, and sugars, preventing the settling and/or rising to the surface of the beads in the mixture,
   c) optionally, at least one other active principle or mixture of beads containing an active principle, and
   d) a suitable amount of water to adjust the viscosity of the composition, and
3) lyophilizing the paste obtained.

17. The process of claim 16, wherein the paste is portioned out into cells of predetermined shape and size prior to lyophilization calculated so as to obtain a defined amount of the active principle or principles in each single dose.

18. The process of claim 16, wherein the lyophilized product is divided into single doses of predetermined shape and size calculated so as to obtain a defined amount of the active principle or principles in each single dose.

* * * * *